US009956391B2

(12) United States Patent
Weissberg et al.

(10) Patent No.: US 9,956,391 B2
(45) Date of Patent: May 1, 2018

(54) ELECTRIC PULSE GENERATORS

(71) Applicant: Pulse Biosciences, Inc., Burlingame, CA (US)

(72) Inventors: Jack Robert Weissberg, Culver City, CA (US); Sudeep Deshpande, Los Angeles, CA (US); Chunqi Jiang, Culver City, CA (US)

(73) Assignee: Pulse Biosciences, Inc., Hayward, CA (US)

( * ) Notice: Subject to any disclaimer, the term of this patent is extended or adjusted under 35 U.S.C. 154(b) by 0 days. days.

(21) Appl. No.: 13/710,077

(22) Filed: Dec. 10, 2012

(65) Prior Publication Data

US 2013/0150935 A1    Jun. 13, 2013

Related U.S. Application Data

(60) Provisional application No. 61/569,667, filed on Dec. 12, 2011.

(51) Int. Cl.
*A61N 1/32* (2006.01)
*A61N 1/04* (2006.01)
*A61N 1/05* (2006.01)

(52) U.S. Cl.
CPC ......... *A61N 1/0468* (2013.01); *A61N 1/0502* (2013.01); *A61N 1/32* (2013.01); *A61N 1/0476* (2013.01); *A61N 1/328* (2013.01)

(58) Field of Classification Search
CPC .... A61N 1/05; A61N 1/36178; A61N 1/0551; A61N 1/056; A61N 1/36189; A61N 1/06; A61N 1/40

USPC .................................................... 607/116, 72
See application file for complete search history.

(56) References Cited

U.S. PATENT DOCUMENTS

| | | | | |
|---|---|---|---|---|
| 5,515,848 A | * | 5/1996 | Corbett, III | A61F 11/04 600/377 |
| 5,906,634 A | * | 5/1999 | Flynn | A61N 1/3752 607/37 |
| 2004/0068296 A1 | * | 4/2004 | Palti | A61N 1/40 607/2 |
| 2007/0025919 A1 | | 2/2007 | Deem et al. | |
| 2009/0254146 A1 | * | 10/2009 | Bonmassar | A61N 2/02 607/45 |

(Continued)

FOREIGN PATENT DOCUMENTS

WO    2010011408 A1    1/2010

OTHER PUBLICATIONS

International Search Report and Written Opinion of the International Searching Authority (EPO), dated Mar. 5, 2013, for PCT Application PCT/US2012/068808, filed Dec. 10, 2012, entitled "Electric Pulse Generators.".

(Continued)

*Primary Examiner* — Niketa Patel
*Assistant Examiner* — Minh Duc Pham
(74) *Attorney, Agent, or Firm* — Kilpatrick Townsend & Stockton LLP

(57) ABSTRACT

This disclosure relates to an in vivo treatment of a skin lesion of a mammal comprising application of electrical energy to the skin lesion in a form of electrical pulses. At least one electrical pulse is applied. The pulse duration may be at least 1 nanosecond at the full-width-half-maximum. This treatment may prevent at least growth of the lesion.

20 Claims, 9 Drawing Sheets

(56) References Cited

U.S. PATENT DOCUMENTS

| | | | |
|---|---|---|---|
| 2009/0299417 A1* | 12/2009 | Schoenbach | A61N 1/327 607/2 |
| 2010/0204638 A1 | 8/2010 | Hobbs et al. | |
| 2010/0261994 A1 | 10/2010 | Davalos et al. | |
| 2011/0137229 A1 | 6/2011 | Palti et al. | |
| 2012/0109263 A1* | 5/2012 | Kolb | A61N 1/0502 607/72 |
| 2012/0306128 A1* | 12/2012 | Parker | A61N 1/3754 264/614 |

OTHER PUBLICATIONS

French et al., "Conductive versus capacitive coupling for cell electroporation with nanosecond pulses," J. Appl. Phys., No. 106, 074701-1, 2009; doi: 10.1063/1.3238245, 5 pages.

Silve et al., "Control of Current Intensity: Experimental Proofs of The Relevance of Current Density in Biological Cells Permeabilisation Caused by Nanosecond Electric Pulses," Pulsed Power Conference (PPC), 2011, IEEE, doi: 10.1109/PPC.2011.6191681, 6 pages.

\* cited by examiner

Example 13
Skin Lesion
Before Treatment

Example 13
Skin Lesion Cleared
After 2nd Treatment

ELECTRIC PULSE GENERATORS

CROSS-REFERENCE TO RELATED APPLICATIONS

This application is based upon and claims priority to U.S. Provisional Application Ser. No. 61/569,667, filed Dec. 12, 2011, entitled "Electric Pulse Generators and Insulated Tips", the entire content of which is incorporated herein by reference.

TECHNICAL FIELD

This disclosure relates to electrical pulse generators and particularly to electrical pulse generators with insulated applicator tips. This disclosure also relates to treatment of skin lesions by delivery of electric pulses to such lesions.

DESCRIPTION OF RELATED ART

Ultra-short, high-field strength electric pulses may be used in the electroperturbation of biological cells. For example, these electric pulses may be used in treatment of human cells and tissue including tumor cells such as basal cell carcinoma, squamous cell carcinoma and melanoma. For a detailed discussion of such applications, for example, see, Garon et al. "In Vitro and In Vivo Evaluation and a Case Report of Intense Nanosecond Pulsed Electric Field as a Local Therapy for Human Malignancies", Int. J. Cancer, vol. 121, 2007, pages 675-682. The entire content of this publication is incorporated herein by reference.

The voltage induced across a cell membrane may depend on the pulse length and pulse amplitude. Pulses longer than about 1 microsecond may charge the outer cell membrane and lead to opening of pores, either temporarily or permanently. Permanent openings may result in cell death.

Pulses much shorter than about 1 microsecond may affect the cell interior without adversely or permanently affecting the outer cell membrane. Such shorter pulses with a field strength in the range of 10 kV/cm to 100 kV/cm may trigger apoptosis or programmed cell death. Higher amplitude and shorter electric pulses are useful in manipulating intracellular structures such as nuclei and mitochondria.

Nanosecond high voltage pulse generators have been proposed for biological and medical applications. For example, see: Gundersen et al. "Nanosecond Pulse Generator Using a Fast Recovery Diode", IEEE 26.sup.th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Schoenbach et al. "Method and Apparatus for Intracellular Electro-Manipulation", U.S. Pat. No. 6,326,177; Gundersen et al., "Method for Intracellular Modifications Within Living Cells Using Pulsed Electric Fields", U.S. Patent Publication No. 2006/0062074; Kuthi et al., "High Voltage Nanosecond Pulse Generator Using Fast Recovery Diodes for Cell Electro-Manipulation", U.S. Pat. No. 7,767,433; Krishnaswamy et al., "Compact Subnanosecond High Voltage Pulse Generation System for Cell Electro-Manipulation", U.S. Patent Publication No. 2008/0231337; and Sanders et al. "Nanosecond Pulse Generator", U.S. Patent Publication No. 2010/0038971. The entire content of these publications is incorporated herein by reference.

Skin treatment apparatuses are also proposed. For example, see Stern "Apparatus and Method for Treatment of Tissue" U.S. Pat. No. 6,413,255. The entire content of this publication is incorporated herein by reference.

SUMMARY

This disclosure relates to a system for delivery of electrical pulses to a tissue. This system may comprise a pulse generator configured to generate at least one pulse having a duration of no more than 1,000 nanoseconds at the full-width-at-half-maximum. This system may further comprise a pulse delivery device comprising a delivery (e.g. active) electrode and a ground (i.e. return, at or near ground potential) electrode. Each of the delivery electrode and the ground electrode has an outer surface.

At least a portion of the outer surface of the ground electrode, the delivery electrode, or both may be coated with an electrically insulating material to reduce or prevent electrical discharge (arcing) between the electrodes during the delivery of electrical pulses to a tissue. The electrically insulating material has a thickness.

Substantially the entire outer surface of the ground electrode, the delivery electrode, or combination thereof may also be coated with an electrically insulating material. In one embodiment, at least a portion of the outer surface of the at least one ground electrode may be coated with an electrically insulating material. In another embodiment, substantially the entire outer surface of the at least one ground electrode may be coated with an electrically insulating material. In yet another embodiment, the entire outer surface of the at least one ground electrode may be coated with an electrically insulating material. The system may also have more than one ground electrode (i.e. multiple ground electrodes) and each of the ground electrodes may have an outer surface. In this embodiment, at least a portion of each outer surface of each ground electrode may be coated with an electrically insulating material.

Said electrically insulating material may be thick enough to reduce or prevent electrical arcing between the at least one delivery electrode and the at least one ground electrode. The thickness of the said electrically insulating material may be at least 1 nanometer, 10 nanometers, 100 nanometers, or 1,000 nanometers.

The insulating material may comprise fluoropolymer, parylene, polyimide, ceramic, glass or composites thereof. In one embodiment, the fluoropolymer is a polytetrafluoroethylene, such as Teflon.

The system may be configured to generate at least one pulse of a duration of no more than 100 nanoseconds at the full-width-at-half-maximum. The system may be configured to generate at least one pulse with an amplitude of at least 1 kV. The electric field formed by the pulses may be at least 1 kV/cm.

In one embodiment, the at least one delivery electrode and/or the at least ground electrode may be configured to partially or substantially penetrate the tissue. In another embodiment, the at least one delivery electrode and/or the at least one ground electrode may be configured not to substantially penetrate a tissue. In yet another embodiment, the at least one ground electrode may be configured not to substantially penetrate a tissue.

The pulse delivery device may also comprise an electrode array. The electrode array may comprise at least two delivery electrodes and at least two ground electrodes.

This disclosure also relates to a treatment of a skin lesion of a mammal comprising application of electrical energy to the skin lesion in the form of at least one electrical pulse by using the system. Multiple pulses may also be applied. The pulse duration may be no longer than 1,000 nanoseconds at the full-width-half-maximum. The energy may be applied in a manner that may prevent at least growth of the lesion.

The skin lesion may be any deviation of skin from a healthy or a normal condition. Examples of skin lesions include skin diseases, conditions, injuries, defects, abnormalities or combinations thereof. For example, such skin lesions include malignancies (such as basal cell carcinomas, squamous cell carcinomas and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrocordon) or combinations thereof. In one embodiment, the skin lesion is basal cell carcinoma, papilloma, squamous cell carcinoma, actinic keratosis, warts or combinations thereof. The skin lesion may also comprise common warts. Or the skin lesion may also comprise actinic keratosis.

The applied electrical energy may be sufficient to prevent growth of the skin lesion for a duration of at least one week after the treatment. The applied electrical energy may be sufficient to reduce the skin lesion volume by at least 30% within eight days after the treatment. The skin lesion volume reduction may be at least 50% or even be at least 80%. The applied electrical energy may be sufficient to clear the skin lesion within eight days after the treatment. The applied energy may be sufficient to reduce the skin lesion volume within eight days after the treatment for at least 80% of cases. The applied energy may be sufficient to reduce the skin lesion volume by at least 30% within eight days after the treatment for at least 80% of cases. The applied energy may eliminate (i.e. clear) the skin lesion.

The duration of the at least one electrical pulse at the full-width-half-maximum may be in the range of 1 nanosecond to 100 nanoseconds. The duration of the at least one electrical pulse at the full-width-half-maximum may be in the range of 1 nanosecond to 30 nanoseconds.

The applied electrical energy may be at least 65 mJ per $mm^3$ of the skin lesion. It may also be at least 260.0 $mJ/mm^3$ or at least 520.0 $mJ/mm^3$.

The system may generate at least one electrical pulse with an amplitude of at least 1 kV. This pulse forms an electric field between the at least one delivery electrode and the at least one ground electrode. The electric field formed by each pulse may be at least 1 kV/cm at the peak amplitude of the pulse. The electric field formed by each pulse may be in the range of 1 kV/cm to 1,000 kV/cm at the peak amplitude of the pulse. The electric field formed by each pulse may be in the range of 1 kV/cm to 100 kV/cm at the peak amplitude of the pulse. The electric field formed by each pulse may be in the range of 10 kV/cm to 50 kV/cm at the peak amplitude of the pulse.

The system may apply at least 10 pulses, 100 pulses or 1,000 pulses.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings disclose illustrative embodiments. They do not set forth all embodiments. Other embodiments may be used in addition or instead. Details which may be apparent or unnecessary may be omitted to save space or for more effective illustration. Conversely, some embodiments may be practiced without all of the details which are disclosed. When the same numeral appears in different drawings, it refers to the same or like components or steps.

DETAILED DESCRIPTION OF ILLUSTRATIVE EMBODIMENTS

Figure 1:
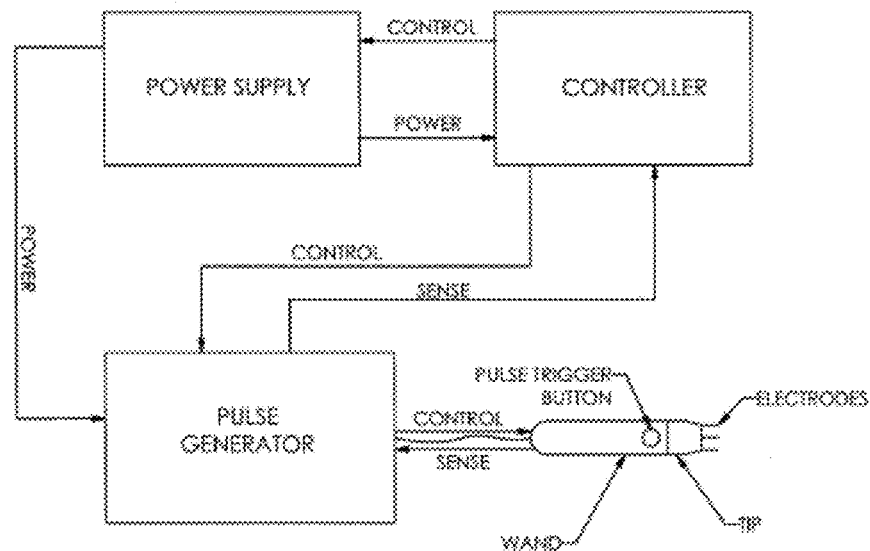
FIG. 1: Example of a system for generation and delivery of electrical nanopulses to a skin lesion.

Illustrative embodiments are now discussed. Other embodiments may be used in addition or instead. Details which may be apparent or unnecessary may be omitted to save space or for a more effective presentation. Conversely, some embodiments may be practiced without all of the details which are disclosed.

This disclosure relates to an in vivo treatment of skin lesions of mammals by application of at least one electrical pulse with duration of 1,000 nanoseconds or less as measured at the full-width-half-maximum (FWHM) of the pulse wave.

The skin lesion that may be treated in vivo by the devices described herein may be any deviation of skin from a healthy or a normal condition. Examples of the skin lesions include skin diseases, conditions, injuries, defects, abnormalities or combinations of thereof. For example, such skin lesions may be malignancies (such as basal cell carcinomas, squamous cell carcinoma and melanoma), precancerous lesions (such as actinic keratosis), human papilloma virus (HPV) infected cells (such as verruca vulgaris or common warts, plantar warts, genital warts), immune-related conditions (such as psoriasis), other skin abnormalities (such as seborrheic keratosis and acrocordon) and combinations thereof. The skin lesion may also include aged skin, wrinkled skin or damaged skin. An example of the damaged skin is the skin damaged by sun radiation. In one embodiment, the skin lesions may be basal cell carcinoma (including papilloma), squamous cell carcinoma, actinic keratosis, warts, or combinations thereof. In one embodiment, the skin lesion may be a skin lesion of a human. In this embodiment, the skin lesion may comprise basal cell carcinoma, squamous cell carcinoma, actinic keratosis, warts, or combinations thereof. In this embodiment, the skin lesion may also comprise common warts, actinic keratosis, or combinations thereof. The skin lesion may be a common wart of a human. The skin lesion may also be an actinic keratosis of a human.

The in vivo treatment may be achieved by providing electrical energy to the skin lesion in a form of electrical pulses. During this treatment, tissue removal may not be intentional and, if it happens, may not be substantial. Thus, the treatment may thereby be advantageous over current or other proposed treatment techniques, since it may achieve its purpose with no substantial tissue removal.

The in vivo treatment of the skin lesion may prevent growth of the lesion. In one embodiment, the treatment may reduce the volume of the skin lesion. That is, the treatment may induce shrinkage of the lesion. This shrinkage may be at least 10%, 20%, 30%, 60%, 70%, 80%, or 90%. Yet, in another embodiment, it may be a treatment to reduce the skin lesion volume to a negligible level (i.e. clearance of the lesion). In yet other embodiments, the lesion growth prevention or the lesion volume reduction may be achieved in at least 10%, 20%, 30%, 40%, 50%, 60%, 70%, 80%, or 90% of the cases.

When the lesion volume shrinks to a negligible size (i.e. about 100%), the lesion is "cleared". If the lesion growth or shrinkage is less than 10% after the treatment, the lesion growth is considered to have been "prevented" or that there is "no change". If the lesion shrinkage is in the range of >10% and <50%, it is concluded that there is lesion "shrinkage". If the lesion shrinkage is in the range of >50% and <100%, it is concluded that there is "substantial shrinkage". If the lesion growth is in the range of >10% to <100%, it is concluded that there is lesion "growth". And if the lesion growth is >100%, it is concluded that there is "substantial growth".

The treatment results may be permanent or temporary. In one embodiment, the growth prevention, or the shrinkage or the clearance may last for a duration of at least 7 days, at least 10 days, at least 20 days, at least 30 days, at least 40 days, at least 50 days, at least 60 days, at least 70 days, at least 80 days, at least 90 days, at least 100 days, or at least 110 days.

Any system may be used for delivery of electrical nanopulses with a duration of 1,000 nanoseconds or less at FWHM to the skin lesion.

The system may comprise a power supply, a controller, a pulse generator, and a pulse delivery device (e.g., a wand). An example of this system is schematically shown in FIG. 1.

The pulse generator may be any pulse generator that is capable of generating pulses with a duration of 1,000 nanoseconds or less at FWHM. Examples of such pulse generators are disclosed in Kuthi et al., "High Voltage Nanosecond Pulse Generator Using Fast Recovery Diodes for Cell Electro-Manipulation", U.S. Pat. No. 7,767,433; Sanders et al. "Nanosecond Pulse Generator", U.S. Patent Publication No. 2010/0038971; and Schoenbach et al. "Method and Apparatus for Intracellular Electro-Manipulation", U.S. Pat. No. 6,326,177. The entire content of these patents is incorporated herein by reference.

The pulse delivery device may be any device that can deliver the electrical pulses to the skin lesion. This device may have an applicator tip that may comprise at least one delivery (e.g. active) electrode. This applicator may further comprise at least one ground (i.e. return, at or near ground potential) electrode. In one embodiment, the delivery electrode and/or the ground electrode may penetrate into the skin lesion to deliver the electrical pulses. In another embodiment, the delivery electrode and/or the ground electrode may deliver the electrical pulses without substantially or intentionally penetrating into the skin lesion. For example, the skin lesion may be constricted between the electrodes or the electrodes may only touch the lesion during the delivery of the electrical pulses.

Figure 4A:
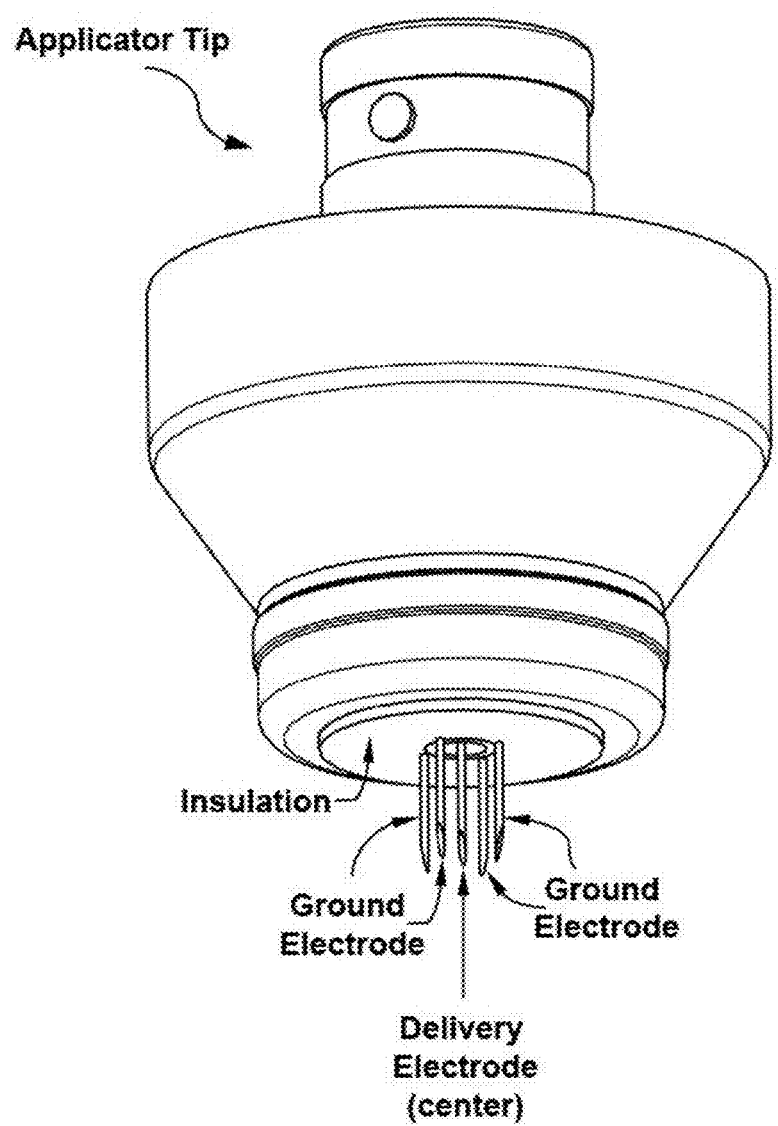
FIG. 4A. Example of an applicator tip with one delivery electrode and four ground electrodes. 4B. A cross sectional view of the exemplary applicator tip shown in FIG. 4A, wherein outer surfaces of the ground electrodes are coated with an electrically insulating material. 4C. A cross sectional view of the exemplary applicator tip shown in FIG. 4A, wherein an outer surface of the delivery electrode is coated with an electrically insulating material. 4D. A cross sectional view of the exemplary applicator tip shown in FIG. 4A, wherein outer surfaces of the delivery electrode and the ground electrodes are coated with an electrically insulating material.

An example of the applicator tip is illustrated in FIG. 4A. In this example, the applicator tip has one delivery electrode placed at the center and four ground electrodes surrounding the delivery electrode. The base of the electrodes may be embedded in a solid insulating material to maintain separations between them.

Other tip configuration may be used instead. There may be other applicator tip configurations suitable for the treatment of the lesions. These configurations may include tips comprising at least one delivery electrode and at least one ground electrode. For example, as the system disclosed above is coaxial in nature, with the ground electrodes surrounding the delivery electrode, any number of needle configurations may be realized, including a circular arrangement with five or more ground electrodes, a triangular arrangement with three ground electrodes, wherein the delivery electrode may be placed at the geometrical center of such arrangements. A simple linear arrangement with just two opposing electrodes, i.e., one return electrode and one delivery electrode, may also be used for the delivery of the electrical pulses.

Still other tip configurations, for example those with different electrode spacing or length, may also be used for the treatment of the lesions. However, as the effect of these short pulses on cells is largely dependent upon the strength of the electric field, an increase in the return and active electrode spacing may have to be accompanied by a proportional increase in output voltage to maintain the required field for the effect on cells. Similarly, if the spacing is reduced, the voltage could be proportionally decreased.

An array of above ground electrode and delivery electrode configurations may also be used to construct a tip and deliver the electrical pulses to the skin lesions. For example, an electrode array comprising at least two delivery electrodes and at least two ground electrodes may be used for this purpose.

Figure 4B:
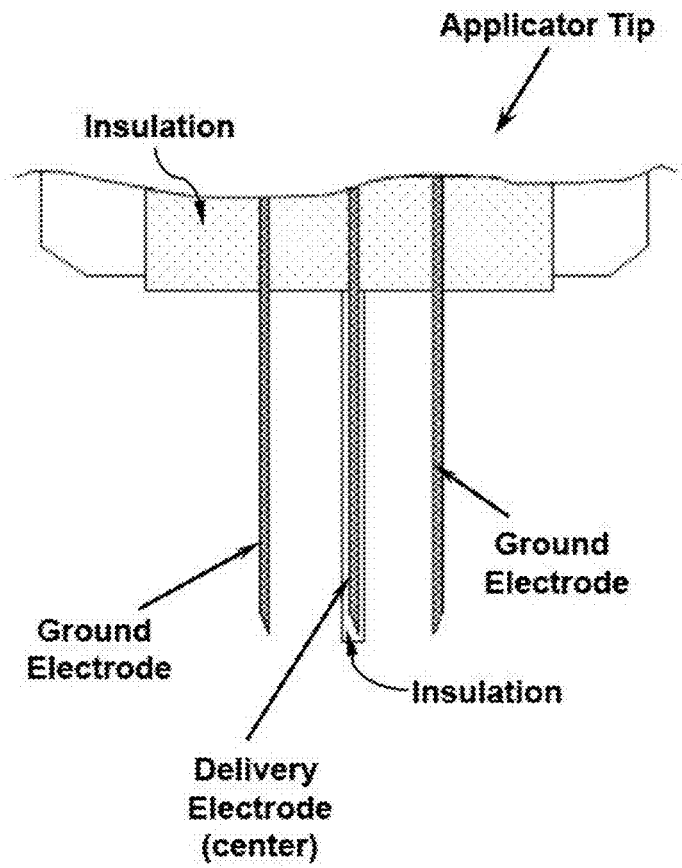
Figure 4C:
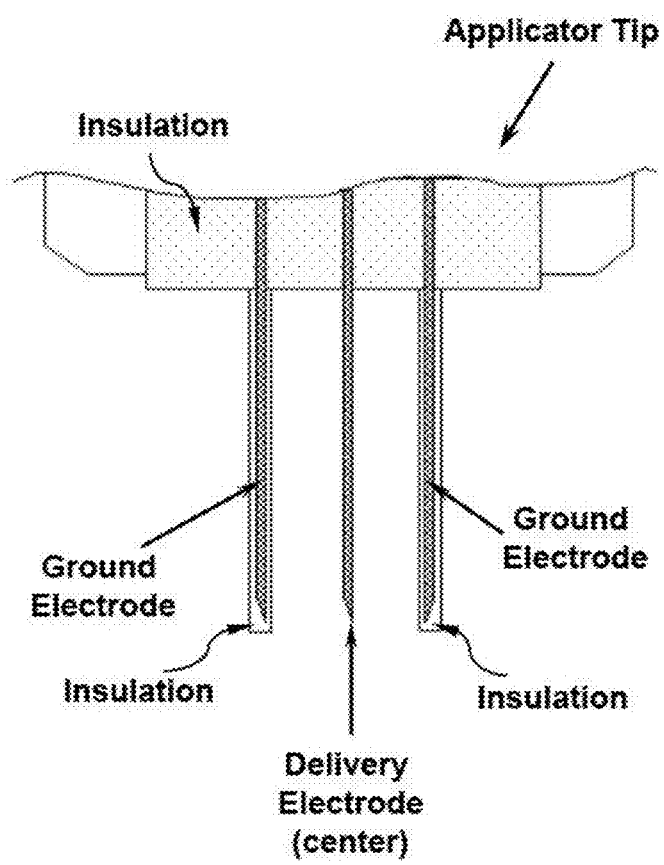
Figure 4D:
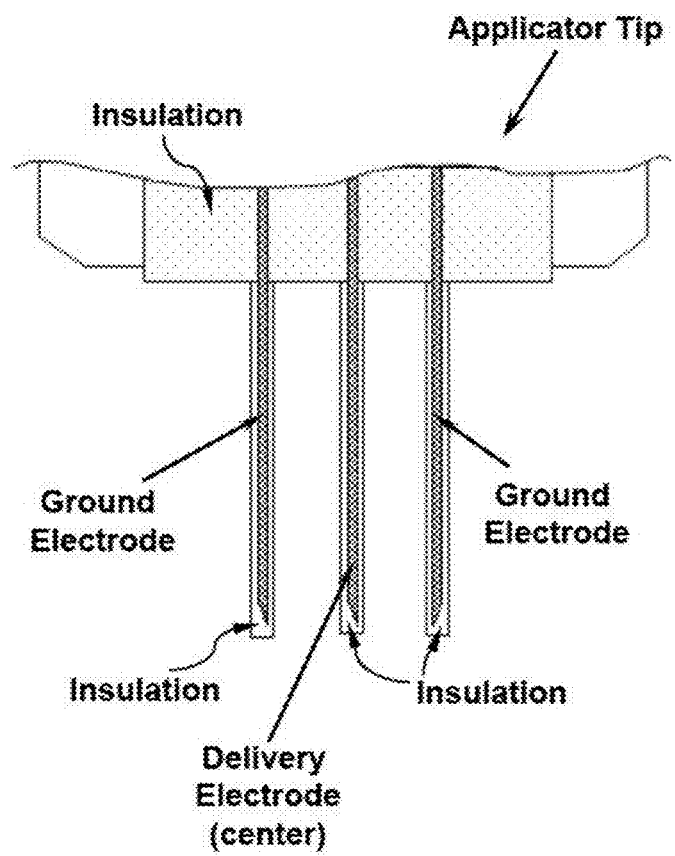

In one embodiment, at least one of the ground electrodes, the delivery electrode, or a combination thereof may be coated with an electrically insulating material. In another embodiment, an outer surface of the ground electrode may be coated with an electrically insulating material. Exemplary applicator tips comprising the coated ground electrodes, the coated delivery electrode, and combinations thereof are shown in FIGS. 4B-4D. The insulating material may coat partially or substantially the entire outer surface of the at least one of the ground electrodes, the delivery electrode, or a combination thereof. The insulating material may also coat the entire outer surface of the at least one of the ground electrodes, the delivery electrode, or a combination thereof. At least a portion of the outer surface or substantially the entire outer surface of the at least one ground electrode may be coated with an electrically insulating material. The entire outer surface of the at least one ground electrode may also be coated with an electrically insulating material. The system may also have more than one ground electrode (i.e. multiple ground electrodes) and each of the ground electrodes may have an outer surface. In this embodiment, at least a portion of each outer surface of each ground electrode may be coated with an electrically insulating material.

The insulating material may comprise a fluoropolymer, parylene, polyimide, ceramic, glass or composites thereof.

The fluoropolymer may be polytetrafluoroethylene. An example of polytetrafluoroethylene is a fluoropolymer commercially manufactured by DuPont under the brand name Teflon.

The insulating electrode coating described above may reduce or even prevent electrical arcing between electrodes. The insulating layer may be thick enough to reduce or prevent electrical arcing between the at least one delivery electrode and the at least one ground electrode, when the electrode is inserted into, pressed against, or brought in very close proximity to the tissue. The thickness of the insulating layer may depend on the material used as the electrically insulating material. This thickness may be experimentally determined. This thickness may also be determined by solving Maxwell equations, for example by using simulation software. An example of this software is COMSOL (Stockholm, Sweden). The thickness of the said electrically insulating material may vary in the range of 1 nanometer to 1 millimeter.

The electrical energy may be applied to the skin lesion in the form of at least one electrical pulse. In one embodiment, at least 10 pulses, at least 100 pulses or at least 1,000 pulses may be applied to treat the lesion during a single treatment.

In one embodiment, the duration of one or more of the pulses at FWHM may be in the range of 0.01 ns to 1,000 ns. The duration of one or more of the pulses at FWHM may also be in the range of 1 ns to 100 ns or in the range of 1 ns to 30 ns. Frequency of pulses may be in the range of 0.1 Hertz (Hz) and 100,000 Hz. The frequency of pulses may also be in the range of 1 Hz to 1,000 Hz.

The electrical energy applied per volume of the skin lesion may be at least 65 mJ/mm$^3$. The applied electrical energy per volume of the skin lesion may also be at least 260 mJ/mm$^3$. In yet another embodiment, the applied electrical energy per volume of the skin lesion may be at least 520 mJ/mm$^3$.

The electric pulse forms an electric field between the at least one delivery electrode and the at least one ground electrode. The formation of this electric field in the tissue may prevent at least the growth of the lesion. This electric field may also cause shrinkage or clearance of the lesion. The electric field formed by each pulse may be at least 1 kV/cm at the peak amplitude of the pulse. The electric field formed by each pulse may also be in the range of 1 kV/cm to 1,000 kV/cm at the peak amplitude of the pulse. Yet, in another embodiment, the electric field formed by each pulse may be in the range of 1 kV/cm to 100 kV/cm at the peak amplitude of the pulse. The electric field formed by each pulse may also be in the range of 10 kV/cm to 50 kV/cm at the peak amplitude of the pulse.

Example 1. Nanopulse Generator and Electrical Nanopulses

An electrical pulse generation and delivery system, schematically shown in FIG. 1, comprising a pulse generator was constructed at the Alfred E. Mann Institute for Biomedical Engineering at the University of Southern California (Los Angeles, Calif.). In this system, the controller provided control signals to both the power supply and the pulse generator. The power supply provided power to both the controller and the pulse generator. And the pulse generator generated the high voltage nanosecond pulses. The wand comprised a pulse trigger button and a tip with electrodes. The pulse trigger button controls the delivery of the pulses from the pulse generator.

Figure 2:
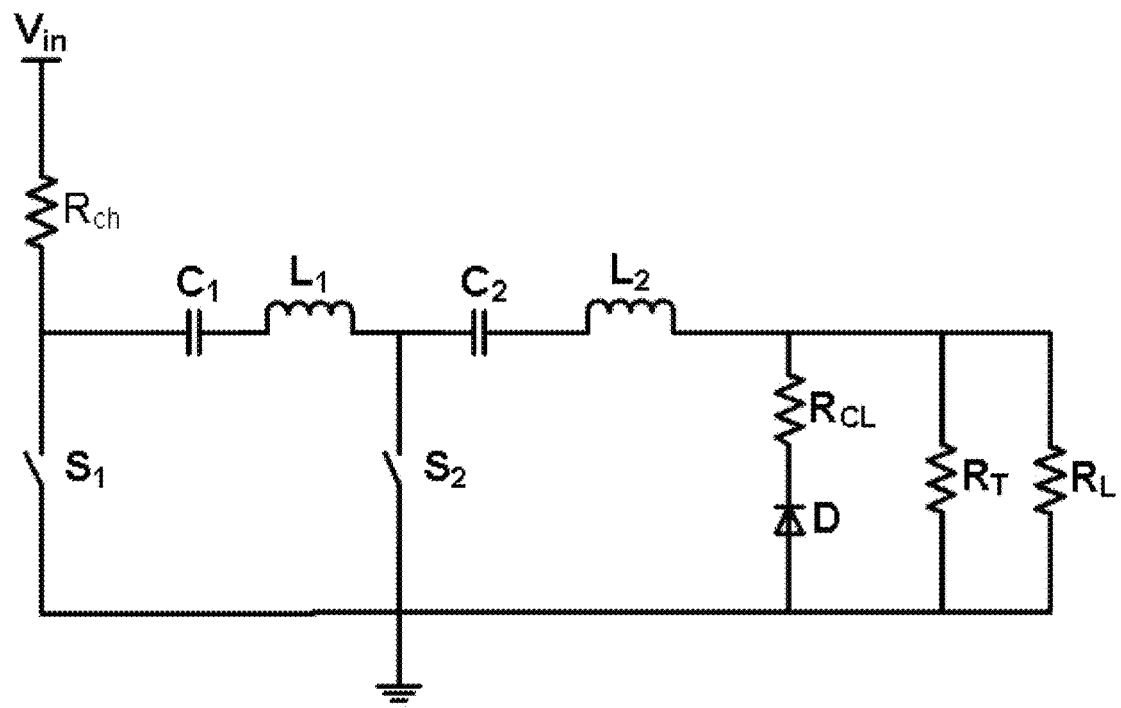
FIG. 2: Example of a simplified diode pulse generator.

An example of the pulse generator is schematically shown in FIG. 2. This pulse generator was previously disclosed in detail in U.S. Pat. No. 7,767,433 to Kuthi et al. and in U.S. Patent Application U.S. 2010/0038971 to Sanders, the content of which is incorporated by reference. This pulse generator is briefly described below.

As shown in FIG. 2, the diode pulse generator may include a tank circuit consisting of inductances $L_1$ and $L_2$ and capacitances $C_1$ and $C_2$. The tank circuit may be connected in series with a diode D across which a load $R_L$ to be driven may be connected. This load is the resistance of the lesion or tissue. The pulse generator may include a switching system, such as switches $S_1$ and $S_2$, which may be electronic. A voltage supply $V_{in}$ may be connected to the diode pulse generator through a resistance $R_{ch}$.

Before the beginning of a pulse cycle, the switch $S_1$ may be open and the switch $S_2$ may be closed. This may cause the capacitance $C_1$ to fully charge and the capacitance $C_2$ to fully discharge.

At the beginning of the pulse cycle, the switch $S_1$ may be closed and the switch $S_2$ may be opened. This may cause charge to transfer from the capacitance $C_1$ to the capacitance $C_2$. During this transfer, the current through the tank circuit may rise and fall in approximately a sinusoidal manner.

This current may cause the diode D to be forward-biased as it travels through it. During this process, charge may be stored in the depletion layer of the diode D.

At the end of the half-cycle, switch $S_2$ may be closed. During the next half-cycle, the current flow may reverse in direction, causing the diode D to be reverse-biased. During the first part of the second half-cycle, current may still flow through the diode D while charge in its depletion layer is being depleted. Once the charge is depleted, the current through the diode D stops, causing the diode to appear as an open switch. This may cause the current through the inductance $L_2$ to commute from the diode D to the load $R_L$. The diode D may thus be configured to act as an opening switch, interrupting the current in the inductance $L_2$ and commuting it into the load $R_L$.

Current may now travel through the load $R_L$ until the energy stored in the tank circuit consisting of the capacitance $C_2$ and the inductance $L_2$ depletes, thus delivering a pulse into the load $R_L$.

This pulse generator included a current limiting resistor, $R_{CL}$ configured to limit damage to the pulse generator. The value of this resistor was about 1 ohm. The pulse generator further included a terminating resistance, $R_T$ in parallel with the diode, wherein the terminating resistance was configured to protect the output stage of the pulse generator. The value of this resistor was about 100 ohms.

Figure 3:
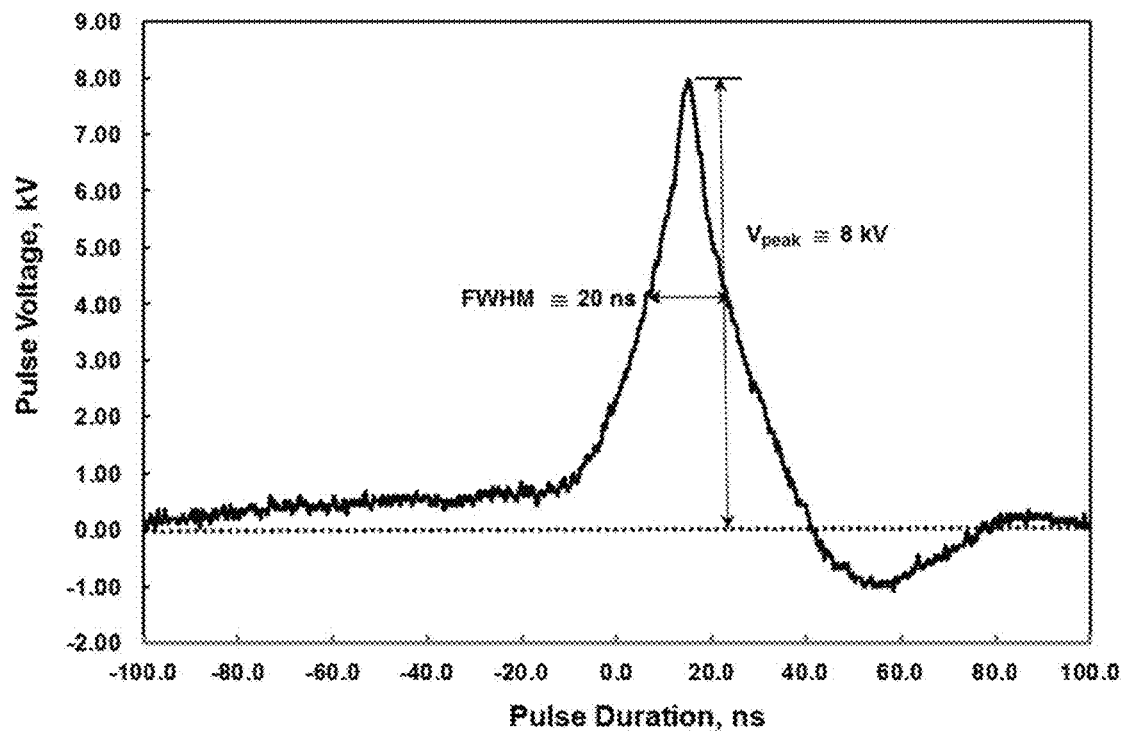
FIG. 3: Example of an electrical pulse generated by the system shown in FIG. 1.

The pulse generator disclosed above provided at least one electrical pulse with a duration varying in the range of about 7 nanoseconds (ns) at FWHM to about 20 ns at FWHM. In one example, a pulse with duration of about 20 ns at FWHM was generated. The characteristics of this pulse were recorded by an oscilloscope manufactured by Tektronix (Beaverton, Oreg.) with a model number of DPO4104. As shown in FIG. 3, this pulse had pulse duration of about 20 ns at FWHM and a peak amplitude of about 8.00 kV.

The electrical nanopulses were delivered to a lesion by using an applicator tip comprising one delivery electrode and four ground electrodes surrounding the delivery electrode. This applicator tip is shown in FIG. 4A. Each electrode was constructed by using a 30 gauge needle (i.e. 0.255 millimeters in diameter). These needles were manufactured by using a 316 LVM implant grade stainless steel material suitable for medical applications. The length of the each electrode was about 5 millimeters (mm). The electrodes were placed to form a square pattern. The ground electrodes were at the corners of this square and the delivery electrode was at its center. The ground electrodes attached to a metal base plate, which also was manufactured by using a 316 LVM implant grade stainless steel material suitable for medical applications. Center-to-center distance between the delivery electrode and each ground electrode was about 1.75 millimeters (mm). This configuration provided a volume of about 30.625 cubic millimeters (mm3) within the boundary formed by ground electrodes. The ground electrodes and the delivery electrode were electrically isolated (i.e. separated) from each other by embedding them in a Teflon insulation, as shown in FIG. 4A.

Outer surfaces of the four ground electrodes were coated with an about 0.127 mm thick PTFE coating, as shown in FIG. 4B. This coating substantially covered the entire outer surface of each of the ground electrodes. The delivery electrode was not coated.

The pulse generator disclosed above provided at least one electrical pulse with duration of about 14 nanoseconds at FHWM. Each pulse with a duration of about 14 nanoseconds at FHWM contained significant frequency components centered at about 71.4 megahertz (MHz). Each such pulse had peak amplitude of about 7.0 kilovolts (kV). These pulses were generated with a frequency of about 50 pulses per second. The electric field was expected to be nominally in the range of 20 kilovolts/centimeter (kV/cm) to 40 kV/cm between the delivery electrode and each of the ground electrode at the peak amplitude of about 7.0 kV.

Values of the pulse durations and the peak amplitudes disclosed in this document were average values unless specifically indicated. These pulse durations and the peak amplitudes may vary with a standard deviation of 10% of their average values. For example, the pulse duration of about 14 ns at FWHM may be an average of pulse durations that vary within the range of 12.60 ns and 15.40 ns, or it is 14.00±1.40 ns. Similarly, the peak amplitude of about 7.00 kV may be an average of the peak amplitudes that vary within the range of 6.30 kV and 7.70 KV, or it is 7.00±0.70 kV.

Electrical power delivered by the applicator tip at the peak of the pulse, $P_{peak}$ is:

$$P_{peak} = V^2_{peak}/R_L \quad \text{Equation 1}$$

where, $V_{peak}$ is peak amplitude of electrical potential. $R_L$ was fixed at about 100 ohms when the pulse generator was configured. That is, the lesion resistance was expected to be about 100 ohms.

And, the electrical energy delivered by the applicator tip per pulse, $E_p$ is:

$$E_p = (2 \times P_{peak} \times t_{FHWM})/3 \quad \text{Equation 2}$$

where, $t_{FHWM}$ is the pulse duration at FWHM.

Then, for RL of about 100 ohms and Vpeak of about 7.00 kV, the total energy delivered to the tissue per pulse was calculated to be about 2.29 millijoules (mJ) for the pulse duration of about 7 ns at FWHM, about 4.57 mJ for the pulse duration of about 14 ns at FWHM, or about 5.88 mJ for the pulse duration of about 18 ns at FWHM. For RL of about 100 ohms and Vpeak of about 5.5 kV, the total energy delivered to the tissue per pulse was calculated to be about 2.82 mJ for the pulse duration of about 14 ns at FWHM.

Example 2. Mouse Model and Formation of Skin Lesions

All experiments with mice were conducted after experimental procedures were approved by the Institutional Animal Care and Use Committee (IACUC) of Department of Comparative Medicine Cedars Sinai Medical Center, Santa Monica, Calif. For all procedures, mice were given isofluorane anesthesia and positioned on a warming bed.

Cutaneous papillomas and squamous carcinomas were chemically induced according to an established protocol disclosed in following publications: Hennings H, Shores R, Mitchell P, Spangler E F, Yuspa S H "Induction of papillomas with a high probability of conversion to malignancy" Carcinogenesis (1985) 6:1607-10; Hennings H, Spangler E F, Shores R, Mitchell P, Devor D, Shamsuddin A K, Elgjo K M, Yuspa S H "Malignant conversion and metastasis of mouse skin tumors: a comparison of SENCAR and CD-1 mice" Environmental health perspectives (1986) 68:69-74; and Slaga T J "SENCAR mouse skin tumorigenesis model versus other strains and stocks of mice" Environmental health perspectives (1986) 68:27-32. The entire content of these publications is incorporated herein by reference.

SENCAR (SENsitivity to CARcinogenesis) and CD-1 mice were used as model animals to induce tumors on their skin and to treat these tumors with electrical nanopulses. SENCAR mice were developed from CD-1 mice by recurrent selection of mice that are sensitive to chemically induced tumor development. SENCAR-A mice (SENCAR A/PtCr) were provided by National Cancer Institute, Frederick, Md. and SENCAR-C mice (SENCAR C/PtJ) were purchased from The Jackson Laboratory, Bar Harbor, Me. CD-1 mice were bought from Charles River Laboratories International Inc., Wilmington, Md. Both SENCAR and CD-1 mice were maintained in Cedars Sinai Medical Center's animal facility.

Carcinogen was applied on the flank of the shaven murine skin using a cotton-tipped applicator. Briefly, tumors were initiated using about two micromoles of methyl-N'-nitro-N-nitrosoguanidine (MNNG) on the first week followed by promotion of the tumor using about two micrograms of 12-O-tetradecanoylphorbol-13-acetate (TPA) which was applied weekly. After 16 to 30 weeks, two to eight tumors (papillomas or carcinomas) were visually detected on each mouse, characterized by rapid growth with elevated margins. These tumors were pink in color and bulbous in appearance.

Based on histology, size and appearance of tumors, about 30% of them were expected to be squamous cell carcinomas showing signs of invasiveness and about 70% were expected to be papillomas. The papillomas are similar to human hypertrophic actinic keratosis (AK). AK is earliest identifiable lesion that may eventually develop into an invasive squamous cell carcinoma (SCC). AK is also clinically quite common and diagnosed in about 14% of all visits to dermatologists. Tumor growth was monitored by measuring size of each tumor using a vernier caliper. Morphology of induced tumors was periodically examined using standard histology.

Examples 3 to 13 Application of Nanosecond Electrical Pulses to Skin Lesions

In Examples 3 to 13, the tumors, which were formed on the mice skin by following the method in the manner of Example 2, were treated by using the nanopulse generator and the insulated applicator tip disclosed in Example 1.

To avoid formation of air pockets between the electrodes, both the tumor and the electrodes were covered with Aquasonic 100 ultrasound transmission gel (Parker Laboratories Inc., Fairfield, N.J., USA). Electrical pulses with varying duration, amplitude and number were delivered to the skin lesion to determine effects of these pulse parameters on tumor treatment.

Figure 5:
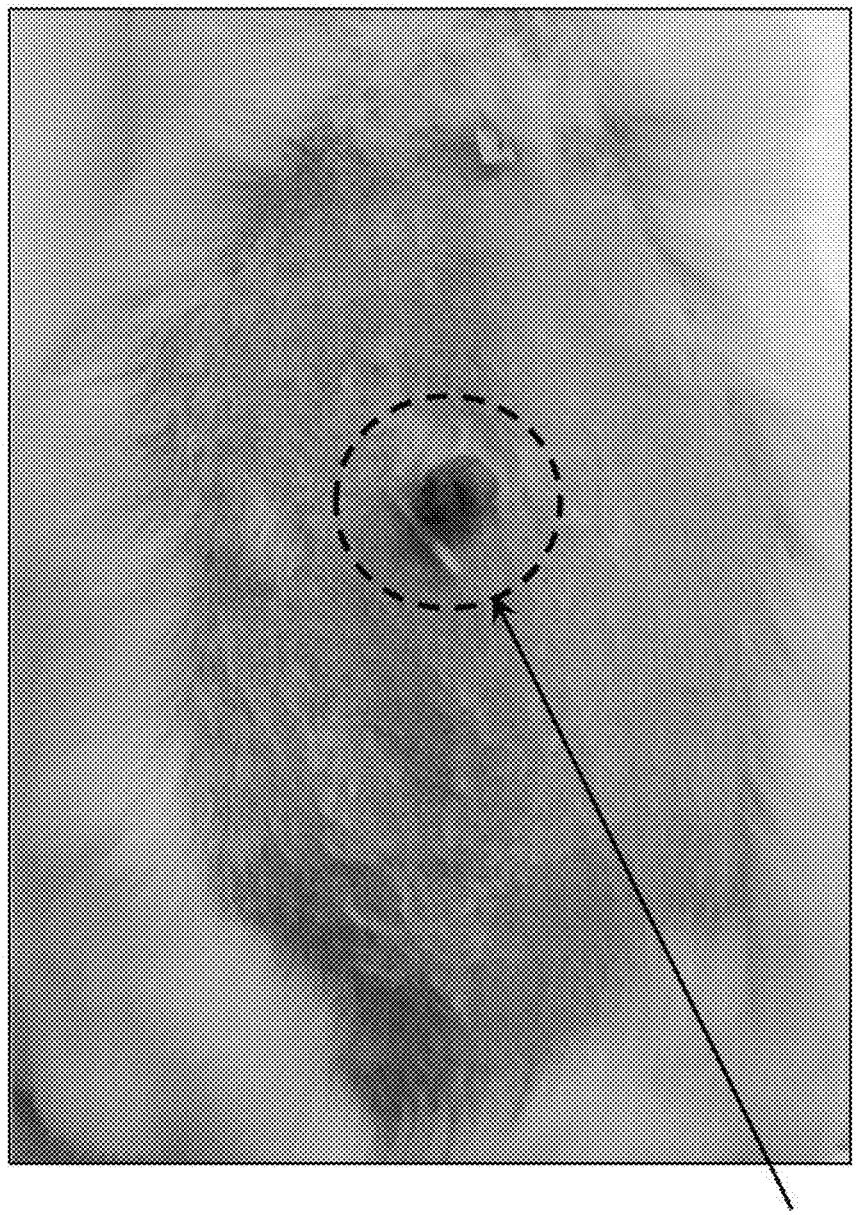
FIG. 5: Photograph of a lesion on a mouse before a treatment.
Figure 6:
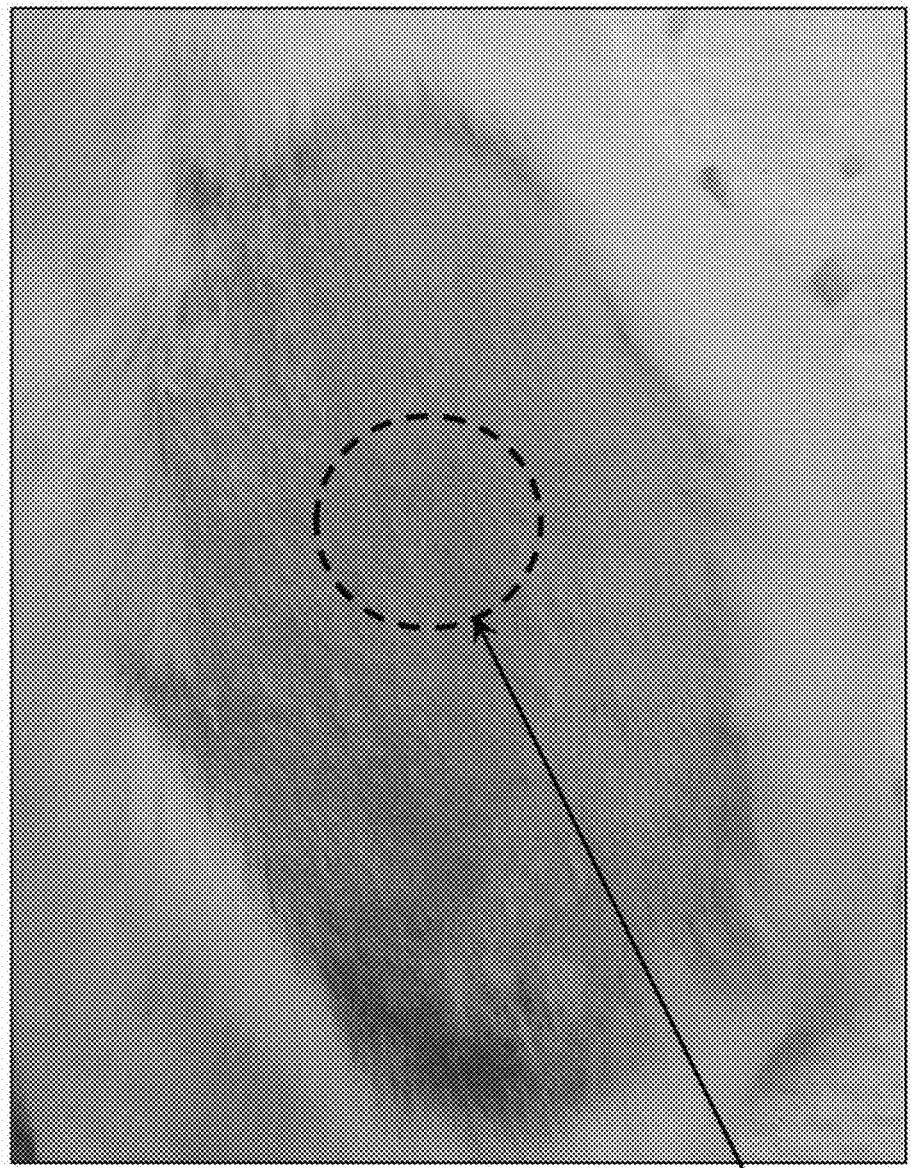
FIG. 6: Photograph of the lesion on the mouse shown in FIG. 5 that was cleared after two treatments.

Photographs of tumors were taken before and after each treatment and also one week after the treatment to record morphology of the tumor, as shown in FIG. 5 and FIG. 6 by way of example.

Tumor size was measured before each treatment and one week after the treatment by using a vernier caliper. The highest elevation of the tumor as measured from the healthy skin surface was recorded as the tumor height. The longest length of the tumor as measured parallel to the healthy skin surface was recorded as the tumor length. For example, before the treatment, the size of the tumor shown in FIG. 5 was about 4.50 mm (length)×about 4 mm (width)×about 4 mm (height) in Example 13.

The widest size perpendicular to the tumor length was recorded as the tumor width. The tumor volume, $T_V$ was then calculated by using the following equation:

$$T_V = 0.625 \times T_L \times T_W \times T_H \qquad \text{Equation 3}$$

where $T_L$ is the tumor length, $T_W$ is the tumor width and $T_H$ is the tumor height. The percent of tumor growth or shrinkage $T_C$ is:

$$T_C = 100 \times (T_{V,after} - T_{V,before}) / T_{V,before} \qquad \text{Equation 4}$$

where $T_{V,after}$ is the tumor volume measured one week after the treatment and $T_{V,before}$ is the tumor volume measured before the treatment.

For example, the volume of the tumor in Example 13 was about 45 mm³ as shown in FIG. 5. After two treatments, the tumor in Example 13 was cleared, i.e. its volume is reduced by about −100%, as shown in FIG. 6 and summarized in Table 1.

The pulse duration at FWHM, the pulse amplitude, and the number of pulses per application were set on the pulse generator. Then, the tumor was slightly elevated from the skin surface by inserting fingers gently under the tumor. Finally, the electrodes were vertically inserted into the tumor and the electrical pulses were applied. Great care was taken to prevent the electrodes from penetrating beyond the height of the tumor. Thus, during the application of the electrical pulses, the electrodes' distal ends were guided so that the electrodes did not penetrate deeper than the measured height of the tumor. For example, if the measured tumor height was about 3.00 millimeters, the penetration depth was also about 3.00 millimeters.

Surface of the tumors, facing the applicator tip, was generally round, but sometimes elliptical or elongated in shape. Locations for insertion of the delivery electrode were visually decided and evenly distributed on this surface. One application was carried out for each millimeter of the tumor length. Tumors shorter than one millimeter in length were not treated. For the tumors which were longer than one millimeter but had lengths that were in fractions of a millimeter where the fractional length was in the range of 0.5 millimeter to 1.0 millimeter, the tumor length was rounded up to calculate the number of applications. For example, for the tumors that had lengths about 5.5 millimeters, 6 applications were carried out.

The center-to-center distance between two opposing ground electrodes was about 3.50 mm. For some tumors, this distance was wider than the width of these tumors. For these tumors, the ground electrodes partially penetrated into the tissue surrounding the tumor.

The total electrical energy delivered by the applicator tip per treatment, $E_T$ is:

$$E_T = E_P \times N_P \times A_N \qquad \text{Equation 5}$$

where $N_P$ is the number of pulses per application and $A_N$ is number of applications per tumor. Electrical energy delivered per volume of tumor, $E_V$ is:

$$E_V = E_T \times T_H / (N_H \times T_{V,before}) \qquad \text{Equation 6}$$

where $N_H$ is the electrode height, which was about 5 millimeters.

Results of experiments carried out to treat skin lesions of mice are summarized in Table 1 to 2. At least two treatments were carried out in each Example. For treatments for which the applied electrical energy is zero, only visual observations were carried out and the electrodes were not inserted into the tumor. In these tables or tables following them, "−" sign in front of the numerals shown in the tumor growth/shrinkage column represent shrinkage of the lesion. For example, "−78%" means 78% shrinkage. If there is no "−" sign in front of the numerals shown in the tumor growth/shrinkage column, it represents growth of the lesion. For example, "43%" means 43% growth.

After the first day following the treatment with electrical nanopulses, the tumors became noticeably darkened, nearly black in some places. This dark hue persisted for about 5 days, after which the color changed to pink and then returned to normal skin color. When the tumor volume shrunk to a negligibly measurable size (i.e. about −100%), this shrinkage was recorded as "tumor cleared". For some tumors, a scab like formation remained although their volume was determined to be negligible one week after the treatment. These scabs were flatter in shape, rough and hard in texture, and red in color. For the scabs, the shrinkage was recorded as "tumor cleared, but scab remained". In some treatments, the tumors did not shrink, but at the same time, they did not grow; that is about 0%. Thus, the tumor growth was prevented. For these treatments, the results were recorded as "tumor volume not changed".

TABLE 1

Electrical pulses applied to skin lesions and treatment results.

| Example | Cage Number | Mouse Number | Tumor Number | Treatment Number | Pulse Duration at FWHM (ns) | Amplitude of Electrical Pulses (kV) | Total Electrical Energy Delivered Per Pulse (mJ) | Number of Electrical Pulses per Application | Number of Applications per Tumor |
|---|---|---|---|---|---|---|---|---|---|
| 3 | 187153 | 1 | 1 | 1 | 14 | 7.00 | 4.57 | 200 | 8 |
|   |        |   |   | 2 | 0  | 0.00 | 0.00 | 0   | 0 |
| 4 | 187151 | 1 | 1 | 1 | 14 | 7.00 | 4.57 | 400 | 8 |
|   |        |   |   | 2 | 0  | 0.00 | 0.00 | 0   | 0 |
|   |        |   |   | 3 | 14 | 7.00 | 4.57 | 400 | 7 |
|   |        |   |   | 4 | 14 | 7.00 | 4.57 | 400 | 7 |
|   |        |   |   | 5 | 14 | 7.00 | 4.57 | 400 | 7 |

TABLE 1-continued

Electrical pulses applied to skin lesions and treatment results.

| | | | | | | | | | |
|---|---|---|---|---|---|---|---|---|---|
| 5 | 187146 | 1 | 1 | 1 | 14 | 7.00 | 4.57 | 400 | 12 |
| | | | | 2 | 0 | 0.00 | 0.00 | 0 | 0 |
| | | | | 3 | 14 | 7.00 | 4.57 | 400 | 4 |
| 6 | 187289 | 1 | 1 | 1 | 14 | 7.00 | 4.57 | 1600 | 3 |
| | | | | 2 | 14 | 7.00 | 4.57 | 1600 | 2 |
| | | | | 3 | 14 | 7.00 | 4.57 | 1600 | 1 |
| | | | | 4 | 14 | 7.00 | 4.57 | 1600 | 4 |
| | | | | 5 | 14 | 7.00 | 4.57 | 1600 | 3 |
| 7 | 187293 | 1 | 1 | 1 | 14 | 7.00 | 4.57 | 1600 | 9 |
| | | | | 2 | 14 | 7.00 | 4.57 | 1600 | 1 |
| | | | | 3 | 0 | 0.00 | 0.00 | 0 | 0 |
| | | | | 4 | 14 | 7.00 | 4.57 | 1600 | 2 |
| | | | | 5 | 14 | 7.00 | 4.57 | 1600 | 1 |
| | | | | 6 | 0 | 0.00 | 0.00 | 0 | 0 |
| 8 | 187293 | 1 | 2 | 1 | 14 | 7.00 | 4.57 | 1600 | 2 |
| | | | | 2 | 14 | 7.00 | 4.57 | 1600 | 1 |
| | | | | 3 | 0 | 0.00 | 0.00 | 0 | 0 |
| 9 | 187155 | 1 | 1 | 1 | 14 | 7.00 | 4.57 | 1600 | 6 |
| | | | | 2 | 14 | 7.00 | 4.57 | 1600 | 2 |
| | | | | 3 | 14 | 7.00 | 4.57 | 1600 | 2 |
| | | | | 4 | 14 | 7.00 | 4.57 | 1600 | 5 |
| | | | | 5 | 14 | 7.00 | 4.57 | 1600 | 5 |
| 10 | 187152 | 1 | 1 | 1 | 14 | 7.00 | 4.57 | 1600 | 4 |
| | | | | 2 | 14 | 7.00 | 4.57 | 1600 | 2 |
| | | | | 3 | 14 | 7.00 | 4.57 | 1600 | 1 |
| | | | | 4 | 14 | 7.00 | 4.57 | 1600 | 1 |
| | | | | 5 | 0 | 0.00 | 0.00 | 0 | 0 |
| 11 | 187152 | 1 | 2 | 1 | 14 | 7.00 | 4.57 | 1600 | 3 |
| | | | | 2 | 14 | 7.00 | 4.57 | 1600 | 3 |
| | | | | 3 | 14 | 7.00 | 4.57 | 1600 | 2 |
| | | | | 4 | 14 | 7.00 | 4.57 | 1600 | 4 |
| | | | | 5 | 14 | 7.00 | 4.57 | 1600 | 4 |
| 12 | 187293 | 2 | 1 | 1 | 14 | 7.00 | 4.57 | 3200 | 2 |
| | | | | 2 | 14 | 7.00 | 4.57 | 3200 | 1 |
| | | | | 3 | 14 | 7.00 | 4.57 | 3200 | 1 |
| | | | | 4 | 0 | 0.00 | 0.00 | 0 | 0 |
| 13 | 187293 | 3 | 1 | 1 | 14 | 7.00 | 4.57 | 3200 | 2 |
| | | | | 2 | 14 | 7.00 | 4.57 | 3200 | 3 |
| | | | | 3 | 0 | 0.00 | 0.00 | 0 | 0 |

| Example | Total Electrical Energy Applied by Tip (mJ) | Electrical Energy Applied per Tumor Volume (mJ/mm$^3$) | Treatment Date (days) | Tumor Size Length (mm) | Width (mm) | Height (mm) | Volume (mm$^3$) | Tumor Growth or Shrinkage (%) | Notes |
|---|---|---|---|---|---|---|---|---|---|
| 3 | 7312.0 | 65.0 | 0 | 6.00 | 6.00 | 4.00 | 90.00 | 0 | Tumor treatment started |
| | 0.0 | 0.0 | 7 | 0.00 | 0.00 | 0.00 | 0.00 | −100 | Tumor cleared |
| 4 | 14624.0 | 83.6 | 0 | 8.00 | 7.00 | 6.00 | 210.00 | 0 | Tumor treatment started |
| | 0.0 | 0.0 | 7 | 7.00 | 6.00 | 5.00 | 131.25 | −38 | Tumor size reduced |
| | 12796.0 | 97.5 | 14 | 7.00 | 6.00 | 5.00 | 131.25 | −38 | Tumor size reduced |
| | 12796.0 | 83.6 | 20 | 7.00 | 7.00 | 5.00 | 153.13 | −27 | Tumor size reduced |
| | 12796.0 | 83.6 | 28 | 7.00 | 7.00 | 4.00 | 122.50 | −42 | Tumor size reduced |
| 5 | 21936.0 | 70.9 | 0 | 11.00 | 9.00 | 8.00 | 495.00 | 0 | Tumor treatment started |
| | 0.0 | 0.0 | 7 | 4.00 | 3.00 | 4.00 | 30.00 | −94 | Tumor size reduced |
| | 7312.0 | 195.0 | 14 | 4.00 | 3.00 | 4.00 | 30.00 | −94 | Tumor size reduced |
| 6 | 21936.0 | 351.0 | 0 | 5.00 | 4.00 | 3.00 | 37.50 | 0 | Tumor treatment started |
| | 14624.0 | 260.0 | 8 | 4.50 | 4.00 | 1.50 | 16.88 | −55 | Tumor size reduced |
| | 7312.0 | 260.0 | 15 | 3.00 | 3.00 | 1.50 | 8.44 | −78 | Tumor size reduced |
| | 29248.0 | 779.9 | 29 | 4.00 | 3.00 | 2.00 | 15.00 | −60 | Tumor size reduced |
| | 21936.0 | 1169.9 | 36 | 3.00 | 2.00 | 1.50 | 5.63 | −85 | Tumor size reduced |
| 7 | 65808.0 | 585.0 | 0 | 9.00 | 4.00 | 5.00 | 112.50 | 0 | Tumor treatment started |
| | 7312.0 | 1559.9 | 8 | 1.50 | 1.00 | 1.00 | 0.94 | −99 | Tumor size reduced |
| | 0.0 | 0.0 | 15 | 1.00 | 1.00 | 0.50 | 0.31 | −100 | Tumor cleared, but scab remained |
| | 14624.0 | 1169.9 | 22 | 2.00 | 2.00 | 1.50 | 3.75 | −97 | Tumor size reduced |
| | 7312.0 | 2339.8 | 29 | 1.00 | 1.00 | 1.00 | 0.63 | −99 | Tumor size reduced |
| | 0.0 | 0.0 | 36 | 0.00 | 0.00 | 0.00 | 0.00 | −100 | Tumor cleared |
| 8 | 14624.0 | 292.5 | 0 | 4.00 | 4.00 | 2.00 | 20.00 | 0 | Tumor treatment started |
| | 7312.0 | 2339.8 | 8 | 1.00 | 1.00 | 1.00 | 0.63 | −97 | Tumor size reduced |
| | 0.0 | 0.0 | 15 | 0.00 | 0.00 | 0.00 | 0.00 | −100 | Tumor cleared |
| 9 | 43872.0 | 390.0 | 0 | 6.00 | 6.00 | 4.00 | 90.00 | 0 | Tumor treatment started |
| | 14624.0 | 170.2 | 8 | 5.50 | 5.00 | 0.50 | 8.59 | −90 | Tumor size reduced |
| | 14624.0 | 260.0 | 15 | 4.50 | 4.00 | 0.50 | 5.63 | −94 | Tumor size reduced |
| | 36560.0 | 577.7 | 29 | 4.50 | 4.50 | 3.00 | 37.97 | −58 | Tumor size reduced |
| | 36560.0 | 779.9 | 36 | 5.00 | 3.00 | 3.00 | 28.13 | −69 | Tumor size reduced |

TABLE 1-continued

Electrical pulses applied to skin lesions and treatment results.

| 10 | 29248.0 | 260.0 | 0 | 6.00 | 6.00 | 5.00 | 112.50 | 0 | Tumor treatment started |
| | 14624.0 | 234.0 | 8 | 5.00 | 4.00 | 4.00 | 50.00 | −56 | Tumor size reduced |
| | 7312.0 | 1039.9 | 15 | 1.50 | 1.50 | 1.50 | 2.11 | −98 | Tumor size reduced |
| | 7312.0 | 9359.4 | 29 | 0.50 | 0.50 | 0.50 | 0.08 | −100 | Tumor cleared, but scab remained |
| | 0.0 | 0.0 | 36 | 0.00 | 0.00 | 0.00 | 0.00 | −100 | Tumor cleared |
| 11 | 21936.0 | 292.5 | 0 | 6.00 | 4.00 | 4.00 | 60.00 | 0 | Tumor treatment started |
| | 21936.0 | 292.5 | 8 | 6.00 | 4.00 | 4.00 | 60.00 | 0 | Tumor volume not changed |
| | 14624.0 | 334.3 | 15 | 4.00 | 3.50 | 4.00 | 35.00 | −42 | Tumor size reduced |
| | 29248.0 | 585.0 | 29 | 4.00 | 4.00 | 3.50 | 35.00 | −42 | Tumor size reduced |
| | 29248.0 | 779.9 | 36 | 4.00 | 3.00 | 2.00 | 15.00 | −75 | Tumor size reduced |
| 12 | 29248.0 | 585.0 | 0 | 4.00 | 4.00 | 3.00 | 30.00 | 0 | Tumor treatment started |
| | 14624.0 | 4679.7 | 7 | 1.00 | 1.00 | 1.00 | 0.63 | −98 | Tumor size reduced |
| | 14624.0 | 18718.7 | 14 | 0.50 | 0.50 | 1.00 | 0.16 | −99 | Tumor size reduced |
| | 0.0 | 0.0 | 21 | 0.00 | 0.00 | 0.00 | 0.00 | −100 | Tumor cleared |
| 13 | 29248.0 | 520.0 | 0 | 4.50 | 4.00 | 4.00 | 45.00 | 0 | Tumor treatment started |
| | 43872.0 | 3509.8 | 7 | 2.00 | 2.00 | 2.50 | 6.25 | −86 | Tumor size reduced |
| | 0.0 | 0.0 | 14 | 0.00 | 0.00 | 0.00 | 0.00 | −100 | Tumor cleared |

The effect of the treatment on the lesion size observed within 8 days after the first treatment was shown in Table 2. When the electrical energy applied per tumor volume was above 65.0 mJ/mm$^3$, the tumor growth was prevented for all eleven cases (e.g. Examples 3 to 13). At this energy level, the lesion size decreased at least 30% for at least 90% of the cases within 8 days after the treatment (e.g. Examples 3 to 13, except Example 11). At above 260.0 mJ/mm$^3$, the size reduction was at least 50% for at least 80% of the cases within 8 days after the treatment (e.g. Examples 6 and 10). And at above 520.0 mJ/mm$^3$, the size reduction was at least 80% for at least 80% of the cases, within 8 days after the treatment (e.g. Examples 7, 12 and 13).

TABLE 2

Electrical pulses applied to skin lesions and treatment results.

| Example | Number of Electrical Pulses per Application | Number of Applications per Tumor | Electrical Energy Applied per Tumor Volume (mJ/mm$^3$) | Treatment Date (days) | Tumor Growth or Shrinkage (%) | Notes |
| --- | --- | --- | --- | --- | --- | --- |
| 3 | 200 | 8 | 65.1 | 0 | 0 | Tumor treatment started |
| | | | | 7 | −100 | Tumor cleared |
| 4 | 400 | 8 | 83.7 | 0 | 0 | Tumor treatment started |
| | | | | 7 | −38 | Tumor size reduced |
| 5 | 400 | 12 | 71.1 | 0 | 0 | Tumor treatment started |
| | | | | 7 | −94 | Tumor size reduced |
| 6 | 1600 | 3 | 351.7 | 0 | 0 | Tumor treatment started |
| | | | | 8 | −55 | Tumor size reduced |
| 7 | 1600 | 9 | 586.2 | 0 | 0 | Tumor treatment started |
| | | | | 8 | −99 | Tumor size reduced |
| 8 | 1600 | 2 | 293.1 | 0 | 0 | Tumor treatment started |
| | | | | 8 | −97 | Tumor size reduced |
| 9 | 1600 | 6 | 390.8 | 0 | 0 | Tumor treatment started |
| | | | | 8 | −90 | Tumor size reduced |
| 10 | 1600 | 4 | 260.6 | 0 | 0 | Tumor treatment started |
| | | | | 8 | −56 | Tumor size reduced |
| 11 | 1600 | 3 | 293.1 | 0 | 0 | Tumor treatment started |
| | | | | 8 | 0 | No size reduction |
| 12 | 3200 | 2 | 586.2 | 0 | 0 | Tumor treatment started |
| | | | | 7 | −98 | Tumor size reduced |
| 13 | 3200 | 2 | 521.1 | 0 | 0 | Tumor treatment started |
| | | | | 7 | −86 | Tumor size reduced |

The components, steps, features, objects, benefits and advantages which have been discussed are merely illustrative. None of them, nor the discussions relating to them, are intended to limit the scope of protection in any way. Numerous other embodiments are also contemplated. These include embodiments which have fewer, additional, and/or different components, steps, features, objects, benefits and advantages. These also include embodiments in which the components and/or steps are arranged and/or ordered differently.

Unless otherwise stated, all measurements, values, ratings, positions, magnitudes, sizes, and other specifications which are set forth in this specification, including in the claims which follow, are approximate, not exact. They are intended to have a reasonable range which is consistent with the functions to which they relate and with what is customary in the art to which they pertain.

All articles, patents, patent applications, and other publications which have been cited in this disclosure are hereby incorporated herein by reference.

Nothing which has been stated or illustrated is intended or should be interpreted to cause a dedication of any component, step, feature, object, benefit, advantage, or equivalent to the public, regardless of whether it is recited in the claims.

We claim:

1. A system for delivery of electrical pulses to tissue comprising:
 a pulse generator configured to generate at least one pulse with an amplitude of at least 1 kV that has a duration of no longer than 1,000 nanoseconds at full-width-at-half-maximum, the pulse generator comprising:
  a tank circuit comprising a first capacitor-inductor pair connected in series with a second capacitor-inductor pair;
  a first switch from a terminal of the circuit to ground; and
  a second switch between the pairs switchable to ground; and
 a pulse delivery device connected with the pulse generator, the pulse delivery device comprising a delivery electrode and a ground electrode spaced apart such that the at least one pulse from the pulse generator produces an electric field between 10 kV/cm and 100 kV/cm between the electrodes, each electrode having an outer surface, wherein the entire outer surface of at least one of the ground electrode or the delivery electrode is coated with an electrically insulating material thick enough to prevent electrical arcing at 10 kV/cm between the delivery electrode and the ground electrode,
 wherein the pulse generator provides the at least one pulse that is generated to the pulse delivery device.

2. The system of claim 1, wherein the entire outer surface of the delivery electrode is coated with the electrically insulating material.

3. The system of claim 1, wherein the entire outer surface of the ground electrode is coated with the electrically insulating material.

4. The system of claim 1, wherein the system includes multiple ground electrodes, each having an outer surface, and
 substantially the entire surface of each outer surface of each ground electrode is coated with the electrically insulating material.

5. The system of claim 1, wherein the electrically insulating material comprises fluoropolymer, parylene, polyimide, ceramic, glass or mixtures thereof.

6. The system of claim 1, wherein the electrically insulating material comprises polytetrafluoroethylene.

7. The system of claim 1, wherein the system is configured to generate at least one pulse that has a duration of no longer than 100 nanoseconds at the full-width-at-half-maximum.

8. The system of claim 1, wherein the delivery electrode is configured to penetrate a tissue.

9. The system of claim 1, wherein the delivery electrode is configured not to substantially penetrate a tissue.

10. The system of claim 1, wherein the ground electrode is configured not to substantially penetrate a tissue.

11. The system of claim 1, wherein the pulse generator is configured to generate the at least one pulse with a duration between 1 nanosecond to 100 nanoseconds.

12. The system of claim 11, wherein the pulse generator is configured to generate the at least one pulse with a duration between 1 nanosecond to 30 nanoseconds.

13. The system of claim 1, wherein the pulse generator is configured to apply at least 10 pulses.

14. The system of claim 1, wherein the pulse delivery device is configured to deliver the at least one pulse to a skin lesion.

15. The system of claim 14, wherein the skin lesion comprises malignancies, precancerous lesions, human papilloma virus (HPV) infected cells, immune-related conditions, seborrheic keratosis, acrocordon, aged skin, wrinkled skin, damaged skin, or combinations thereof.

16. The system of claim 14, wherein the skin lesion comprises basal cell carcinoma, squamous cell carcinoma, actinic keratosis, warts, or combinations thereof.

17. The system of claim 14, wherein the skin lesion comprises common warts, actinic keratosis, or combinations thereof.

18. The system of claim 1, wherein the pulse generator and pulse delivery device are configured to apply electrical energy of at least 65.0 mJ per $mm^3$ to a skin lesion.

19. The system of claim 1, wherein the pulse generator and pulse delivery device are configured to apply electrical energy of at least 260.0 mJ per $mm^3$ to a skin lesion.

20. The system of claim 1, wherein the pulse generator and pulse delivery device are configured to apply electrical energy of at least 520.0 mJ per $mm^3$ to a skin lesion.

* * * * *